United States Patent [19]

John et al.

[11] Patent Number: 5,549,118

[45] Date of Patent: Aug. 27, 1996

[54] SIMULTANEOUS TESTING OF TWO MOTOR CAPABILITIES OF A HUMAN SUBJECT

[75] Inventors: Erwin R. John, Mamaroneck; Paul D. Easton, Long Island City, both of N.Y.

[73] Assignee: New York University, N.Y.

[21] Appl. No.: 125,338

[22] Filed: Sep. 22, 1993

[51] Int. Cl.⁶ ............................................. A61B 5/0484
[52] U.S. Cl. ...................... 128/731; 128/745; 128/746
[58] Field of Search .............................. 128/731–2, 745, 128/746

[56] References Cited

U.S. PATENT DOCUMENTS

| | | | |
|---|---|---|---|
| 3,780,724 | 12/1973 | John | 128/731 |
| 4,201,224 | 5/1980 | John | 128/731 |
| 4,216,781 | 8/1980 | John | 128/731 |
| 4,987,903 | 1/1991 | Keppel et al. | 128/731 X |

*Primary Examiner*—Angela D. Sykes
*Attorney, Agent, or Firm*—Eliot S. Gerber

[57] ABSTRACT

In a computer based system and method for behavior testing of human subjects, the subject is simultaneously presented with stimuli in two modes, for example, a screen showing a moving target spot and a subject controlled pursuer, and also a tone which varies in pitch and changes in amplitude as between left and right earphones. In one embodiment, the subject's brain waves are detected and measured, using an electroencephalograph (EEG) instrument, at the same time the subject is performing the test.

19 Claims, 2 Drawing Sheets

SIMULTANEOUS TESTING OF TWO MOTOR CAPABILITIES OF A HUMAN SUBJECT

BACKGROUND OF THE INVENTION

1. Field of the Invention

The present invention relates to computer based behavior testing of human subjects and more particularly to such testing which monitors the subject's electrical brain-wave activity using an electroencephalograph (EEG) instrument.

2. Related Art

At the present time, the coordination and information processing capabilities of human subjects may be tested using a computer based system. For example, in one device, the subject is asked to engage in a task in which a display is shown on a video monitor while the subject controls a cursor on the screen by operation of a joy stick (control stick). The subject's test score is then compared with the subject's prior test scores to determine if the subject's ability is impaired. Generally that type of system tests eye-hand coordination, but may also test speed of information capacity, i.e., "channel capacity".

It has been suggested that such computer based systems should be used in place of drug testing, which may require urine and/or blood samples.

The purpose of such testing, for example, may be to determine if the subject is within the range of the subject's own normal behavior or if the subject is impaired; or to test the ability of the subject, assuming the subject is alert, to perform eye-hand coordination tasks of the type exemplified by the test.

The present commercially available systems however only test one mode, for example eye-hand coordination, so that the subject may in fact be at least partially impaired or deficient as to functioning in other modes, but such impairment or deficiency will not be detected by the system.

In U.S. Pat. No. 4,158,920 to Walker, entitled "Method And Apparatus For Testing For Brain-Dysfunction In a Human", a subject is tested for brain dysfunction by performing a primary tasking of centering a light spot on a reference point by moving a control stick. Simultaneously, the subject is presented with a secondary task of moving another control stick in response to high or low auditory tones. The subject's responses are recorded on a graph recorder.

In U.S. Pat. No. 4,515,169 to Ward, entitled "Differential Latency Audiometer", an auditory stimulus is directed against the tympanic membrane of the subject's ear to evoke a brain-stem evoked response (BSER). The subject adjusts a latency control knob on the instrument until the sound image is perceived to be in the center of the subject's head. The difference in the latency time is then computed over a set of trials to determine if the subject's differential latency is within the normal range. The use of topographic mapping of brain electrical activity detection using an EEG instrument is illustrated, for example, in U.S. Pat. No. 4,844,086 to Duffy.

SUMMARY OF THE INVENTION

In accordance with the present invention the subject to be tested is seated in front of a video monitor. A software programmed computer system controls the display on the monitor screen and provides an illuminated colored "target" spot which is moved over the face of the screen. The program controls the light intensity of the "target" spot, its direction of movement and its speed of movement. Preferably the direction and speed of movement of the "target" spot are random and its intensity is sinusoidally modulated or gated on and off at some prime frequency $F_1$ in the EEG range, i.e., between 3.0 to 40 Hz.

The subject operates a computer input device, preferably a joy stick which controls the movement of an illuminated "pursuer" on the screen, preferably of a different color than the target spot and an intensity modulated at a different frequency $F_2$ than the target spot, and not a harmonic of $F_1$. The subject attempts to follow and "touch" the target with the pursuer by operating the joy stick. The computer enters into its RAM (Random Access Memory) the position of the target spot, at each moment, and the position of the pursuer. It records the momentary distance of the pursuer from the target and calculates, for each session, the total distance of the pursuer from the target. For example, a session may be 5 to 10 minutes long. The scores of the number of touches of the subject, target-pursuer distance as a function of time, and integrated target-pursuer distances are an indication of the subject's continuous pursuit performance (eye-hand coordination) during the session.

The subject may also be presented with an auditory test, separately or simultaneously with the visual presentation on the video monitor screen. The subject wears a headphone having left and right earphones over the subject's left and right ears. The computer system controls a tone generator which generates a target tone to the left and right earphones, intensity modulated at some prime frequency, $F_3$, not a harmonic of $F_1$ or $F_2$. The intensity of the tone is gradually made faint in one earphone and louder in the other so the subject imagines a "flickering" target auditory image (in auditory space) which moves from one side of the subject's head to the other. At the same time the pitch of the intensity modulated tone rises or falls (higher or lower pitch). The subject, with a second joy stick in the subject's other hand, controls the relative binaural intensity and pitch of a "pursuit beep" (intermittent at a repetition rate $F_4$) with which he attempts to follow the target tone image from side to side (left-right-left etc) and in elevation (up-down-up etc). The target tone forms an imaginary flickering tone image in the subject's head at a small imaginary location in an auditory space, which moves up and down and sideways in accordance with the computer program controlling the rise and fall of the tone and its relative loudness in one earphone or the other. The pursuit beep constitutes a similar but distinct flickering image in auditory space, whose position is controlled by the subject. To recapitulate, the frequency, $F_3$, of the modulation of the target tone is selected to be different from the frequency, modulation of the pursuit, $F_4$, and both have different frequencies from the frequencies of the target spot, $F_1$, and pursuer spot, $F_2$, and their harmonics.

The computer system computes the number of "touches" the subject attains by movement of the second joy stick. A "touch" in this case is the movement of the pursuit beep in auditory space, as represented in the computer memory, to within a predetermined coincident distance of the position of the target tone in auditory space, represented similarly. In addition, the distances between the target and pursuer are recorded as a function of time and also integrated. These calculations provide an auditory test score for each session.

The scores for each subject of the continuous pursuit task separately in visual space, in auditory space, and combined into a task requiring simultaneous but independent visual and auditory pursuit reflect the subject's normal performance capability when his/her ability to coordinate movement with information is simultaneously or separately challenged in two sensory modalities.

The subject's brain waves may be measured during at least one testing session using an EEG instrument. The subject's brain waves, which are analog signals at the microvolt level, are amplified, converted to digital data, and processed by the computer system under program (software) control to compare the power spectrum and coherence/covariance matrix of the subject's brain waves to those of a normative group, of comparative age and sex. The results of such comparisons are displayed on a color coded topographical map of the brain, which highlights brain areas or relationships which are abnormal or normal. The four frequencies of the target spot, pursuer spot, target tone and pursuit beep may be reflected by changes in power at those frequencies in the power spectral analysis of the subject's amplified brain waves and may differ in different brain regions which mediate various aspects of the behavioral performance, reflecting the subject's "cognitive style" in this complex task, as well as the long-term maintenance of attention.

Once the testing of two simultaneous coordination capabilities has been completed and analyzed along with the EEG recording, the subject may be tested subsequently, at other times, without EEG data collection, for example, to evaluate changes with fatigue, with aging or as the result of training.

BRIEF DESCRIPTION OF THE DRAWINGS

Other objectives of the present invention will be apparent from the following detailed description taken in conjunction with the accompanying drawings. In the drawings.

OBJECTIVES AND FEATURES OF THE INVENTION

It is an objective of the present invention to provide a method and system for testing the coordination and information processing capabilities and "cognitive style" of a human subject by challenging the subject in two sensory modes, separately and/or together.

It is a further objective of the present invention to provide a graph of performance versus time and a test score which is the integrated target-pursuer distance accumulated during a test session for each modality for which a target is present and to score the total number of "hits" or "touches" accomplished by the subject in each modality.

It is a further objective of the present invention to provide such a method and system in which the subject's brain waves, during such testing, are measured, compared with a normative group, and the results of such comparison presented in the form of a readily comprehended visual display.

It is a further objective of the present invention that the subject will not be able to cheat on the test.

DETAILED DESCRIPTION OF THE INVENTION

Figure 1:
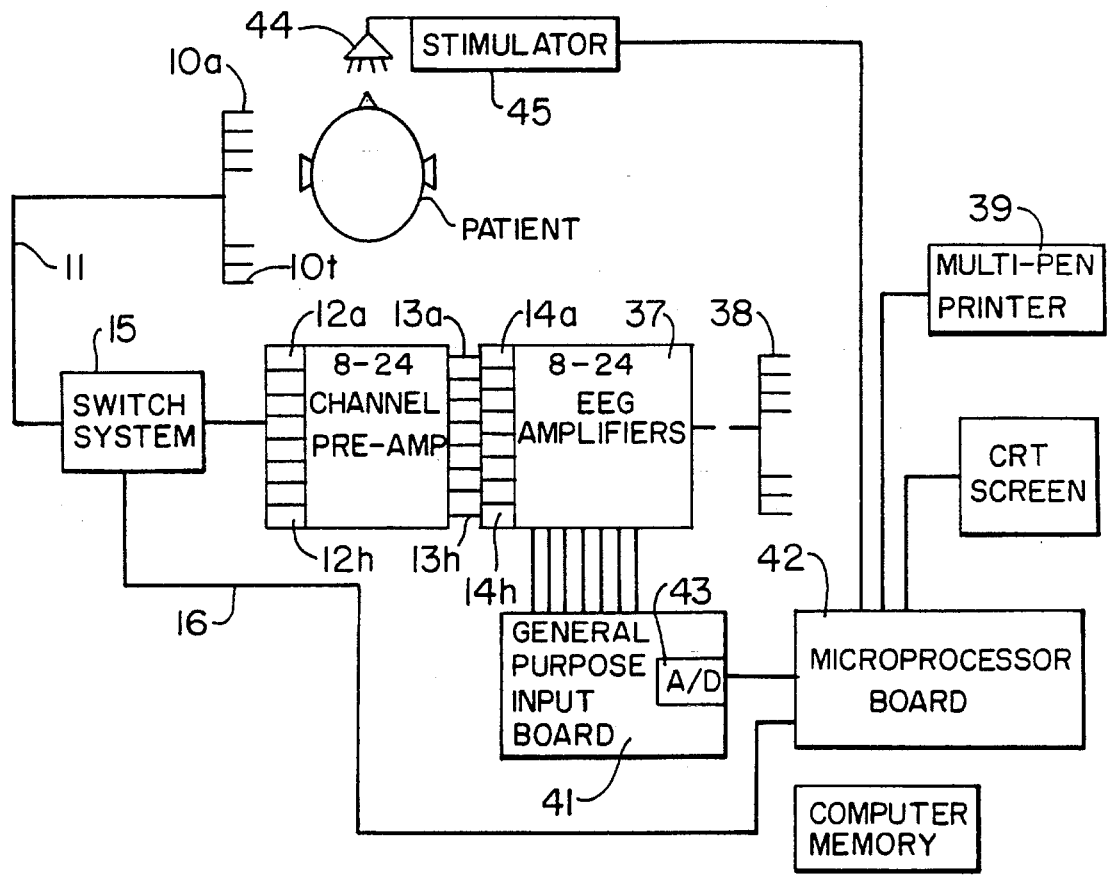
FIG. 1 is a block diagram of the system of the present invention.

FIG. 1 depicts the apparatus of the present invention. The apparatus consists of a video monitor 10, a computer control system 20, a tone generator 60, a pair of headphones 70, an EEG (electroencephalograph) sensor device 90, and one or more input control devices 30 and 40. Alternatively, and not shown, the video monitor, the computer system and the tone generator may all be contained in a single, compact unit. The video monitor 10 presents to the subject 80 a target 50, for example, a lighted disc about 1 cm. in diameter ("target spot" or "target"). The computer system 20 moves the target in at least one dimension, but preferably simultaneously in both the horizontal and vertical directions on the video screen. The computer also controls the luminous intensity of the target, its speed of movement on the screen and its frequency of flashing, $F_1$. Preferably the flashing, $F_1$, is a sinusoidal modulation at 3–40 Hz, depending upon the critical fusion frequency (CFF) of the subject. A pursuit cursor 55 ("pursuer"), preferably of a different color, also appears on the monitor 10, where, for example, the cursor is a short vertical line or a disc of a different color. The cursor is controllable by the subject 80 by means of an input control device 30 which is typically a joystick or trackball. The intensity of the pursuer is modulated at a second frequency, $F_2$, different from the frequency of the target; preferably a sinusoidal modulation at 3.0–40 Hz.

The computer system 20 continuously monitors the positions of the target 50 and the pursuer 55. The integrated distance between the target and the pursuer is calculated continuously for each target modality and is displayed and updated constantly on the screen. This distance is also recorded as a function of time, which can be displayed as a line graph. The computer program calculates the number of "touches" the test subject scores by bringing the pursuer to within a predetermined distance of the target, for example, to within 0.5 cm.

The computer system 20 also controls a tone generator 60 which presents the test subject 80 with auditory stimuli through a pair of headphones 70. The tone generator 60 creates target tones, warbling in intensity at some modulation frequency, $F_3$, and charging in relative intensity between the right and left earphones. The position of the tone may be varied between imaginary points (auditory space) inside the test subject's head as a function of the relative amplitude (loudness) of the tone in each earphone. The frequency (pitch) of the tone also rises and falls in a controlled manner to indicate vertical position in the auditory space. The test subject 80 uses a second input control device 40, such as a second joy stick or second trackball, to track the position of the tone (left-right location in the auditory space) as well as its pitch (up-down location) by varying the pitch and relative left-right amplitude of intermittent "pursuer" beeps at frequency $F_4$. The integrated distance between target tone and pursuer beeps is continuously updated and displayed on the screen. This distance as a function of time can also be displayed. The computer system 20 calculates the number of "hits" or "touches" the test subject 80 scores with the second input control device 40. A touch in this case would correspond to the movement of the imaginary audio pursuer, in computer memory, to within a predetermined distance, in imaginary auditory space, of the position of the tone, as determined by the amplitude and frequency of the tones in the left and right earphones. The computer also calculates the reaction time of the test subject in tracking the position of the audio tone.

The test subject 80 is further tested by the simultaneous measurement of eye-hand and ear-hand coordination. This is accomplished by having the test subject 30 track the video target 50 with input control device 30, while at the same time tracking the position of the tone with the input control device 40. Again the computer system integrates visual and auditory target-pursuer distances, or displays these as two continuous curves versus time, calculates the number of video and audio "touches" scored by the test subject as well as the time required for the test subject to score the "touch" after each change in the position of the video target or audio tone.

The computer system 20 may also perform the task of measuring the EEG signals of the test subject 80 while the test subject is performing either the video tracking test, the audio tracking test, or preferably both. A plurality of EEG electrode sensors 100 are removably attached to the head of the test subject 80. The electrode sensors detect brain wave activity which is measured by the EEG sensor device 90. Artifact detection means for EOG (eye movement) and EMG (head and neck muscles) sense contamination of the EEG by non-brain electrical activity and reject such contaminated activity from analysis procedures. Initially, the EEG sensor device 90 amplifies the received brain wave signals in a high impedance, fixed gain amplifier stage 95. The amplified signals are then converted by the EEG sensor device to a digital signal in a variable gain analog-to-digital converter (A/D) stage 96. The gain of the A/D converter stage is controllable by the computer system 20.

Figure 3:
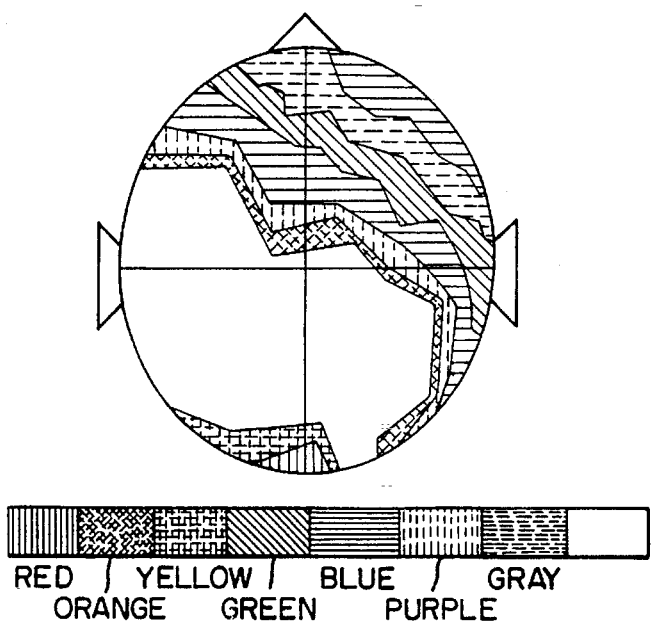
FIG. 3 is a sample of a topographical head map.
Figure 2:
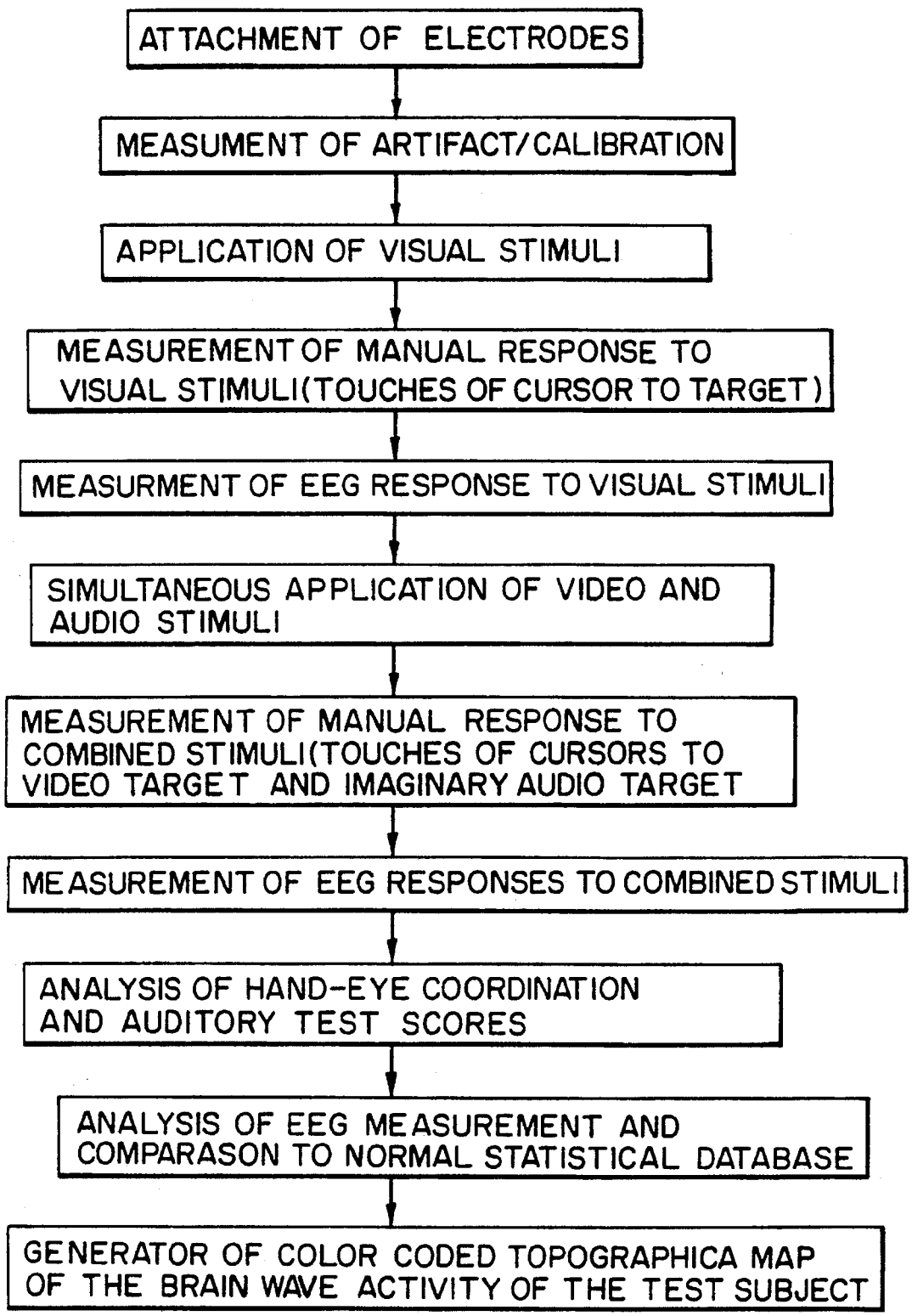
FIG. 2 is a flow chart of a typical testing session.

The EEG electrode leads may be attached to various points on the test subject's head. The International 10/20 electrode system and nomenclature is the preferred method. The computer system 20 analyzes the measured EEG brain wave signals by spectral analysis and can generate representations of the difference between two measured EEG responses, for example, population or individual recordings at rest versus during task performance, and may produce color coded topographical maps of the test subject's head 80, as shown in FIG. 3. The measured waveforms, the difference spectra generated by the computer system 20, and the topographical headmaps produced by the computer system 20 may be displayed on an output device such as a conventional video monitor 105 or printer 100 for "hard copies" of test results. Integrated target-pursuer distances for specific parametric values of target trajectory velocity and complexity, as well as the measured brain waves, and the difference waveforms and topographical head maps generated by the computer system 20 can be compared to a data base of normal responses for a control group of similar age and sex.

The age and sex of the subject are entered into the computer system 20 by the operator using keyboard 115.

The apparatus and methods for the EEG analysis are found in the inventor's U.S. Pat. No. 4,913,160 entitled "Electroencephalographic System And Method Using Factor Structure Of The Evoked Potentials" and U.S. Pat. No. 4,846,190 entitled "Electroencephalographic System Data Display", both are incorporated by reference herein.

What is claimed is:

1. An apparatus for testing and analyzing the evoked brain activity and motor responses of a subject to simultaneous stimuli in two different modes, the modes being selected from visual, audio and tactile responses, the apparatus comprising:

a) a first means to present programmed stimuli in a first mode to the subject the stimuli in a first mode having been programmed in advance of the presentation thereof;

b) a second means to simultaneously present programmed stimuli in a second and different mode to the subject, the stimuli in a second mode having been programmed in advance of the presentation thereof;

c) a plurality of EEG (electroencephalograph) sensor adapted to be removably attached to the subject's head for measuring analog brain wave electrical activity;

d) amplification means for amplifying the measured analog brain wave electrical activity;

e) an A/D (analog/digital) converter means to convert the amplified brain wave electrical activity to digital data;

f) a first and a second operator control means, each being adapted to be controlled by the subject in response to the simultaneous stimuli in two modes;

g) a computer means for controlling the first means and second means for simultaneously presenting to the subject independently previously programmed controllable stimuli in two different modes, for measuring the motor response of the subject to the test stimuli, for recording the evoked brain wave digital data of the subject in response to the stimuli, for analyzing the motor responses and evoked brain wave digital data, for comparing the motor responses and evoked brain wave digital data to a data base of normal test results stored in a memory of the computer means, and for producing a visual display of the test results;

wherein the A/D means is a variable gain analog-to-digital conversion means for digitizing the amplified analog brain wave electrical activity and wherein the variable gain of the A/D converter is controlled by the computer means.

2. An apparatus for testing and analyzing the evoked brain electrical activity and motor responses of a subject to simultaneous stimuli in two different modes, the first mode being visual stimuli and the second mode being auditory stimuli;

a) a screen means to present the visual stimuli to the subject and an audio means to present the auditory stimuli to the subject;

b) a first means to present programmed stimuli in the first mode to the subject, the stimuli in the first mode having been programmed in advance of the presentation thereof;

c) a second means to simultaneously present programmed stimuli in the second mode to the subject, the stimuli in a second mode having been programmed in advance of the presentation thereof;

d) a plurality of EEG (electroencephalograph) sensors adapted to be removably attached to the subject's head for measuring analog brain wave electrical activity;

e) amplification means to amplify the measured analog brain wave electrical activity;

f) an A/D (analog/digital) converter means to convert the amplified brain wave electrical activity to digital data;

g) a first and a second operator control means, each being adapted to be controlled by the subject in response to the simultaneous stimuli in the two modes;

h) a computer means for controlling the first means and second means for simultaneously presenting to the subject independently previously programmed controllable stimuli in the different modes, for measuring the motor response of the subject to the test stimuli, for recording the evoked brain wave digital data of the subject in response to the stimuli, for analyzing the motor responses and evoked brain wave digital data, for comparing the motor responses and evoked brain wave digital data to a data base of normal test results stored in a memory of the computer means, and for producing a visual display of the test results;

i) wherein the screen displays a visible and movable target spot and a visible and movable tracking cursor, the target spot being controllable by the computer means and the cursor being controllable by the first operator control means.

3. An apparatus as in claim 2 the first operator control means comprises a control stick means for positioning the tracking cursor on the screen, wherein the computer means receives the cursor movement signals from the control stick means and moves the cursor a corresponding distance on the screen.

4. An apparatus as in claim 2 wherein the target spot and cursor each have an intensity and the apparatus includes means to vary the intensity of the target spot at one frequency and vary the intensity of the cursor at a different frequency, both frequencies being in the 3–40 Hz band.

5. An apparatus for testing and analyzing the evoked brain electrical activity and motor responses of a subject to simultaneous stimuli in two different modes, a first mode being visual stimuli and a second mode being audio stimuli;
   a) a screen means to present the visual stimuli to the subject and an audio means to present the auditory stimuli to the subject;
   b) a first means to represent programmed stimuli in the first mode to the subject, the stimuli in the first mode having been programmed in advance of the presentation thereof;
   c) a second means to simultaneously present programmed stimuli in the second mode to the subject, the stimuli in a second mode having been programmed in advance of the presentation thereof;
   d) a plurality of EEG (electroencephalograph) sensors adapted to be removably attached to the subject's head for measuring analog brain wave electrical activity;
   e) amplification means to amplify the measured analog brain wave electrical activity;
   f) an A/D (analog/digital) converter means to convert the amplified brain wave electrical activity to digital data;
   g) a first and a second operator control means, each being adapted to be controlled by the subject in response to the simultaneous stimuli in the two modes;
   h) a computer means for controlling the first means and second means for simultaneously presenting to the subject independently previously programmed controllable stimuli, in the two different modes, for measuring the motor response of the subject to the test stimuli, for recording the evoked brain wave digital data of the subject in response to the stimuli, for analyzing the motor responses and evoked brain wave digital data, for comparing the motor responses and evoked brain wave digital data to a data base of normal test results stored in a memory of the computer means, and for producing a visual display of the test results;
   i) wherein the audio means includes a pair of headphones having left and right earphones and a tone generator means for presenting an audio signal to the subject through a pair of headphones, the audio signal being controllable in amplitude and frequency by the computer means, the difference in amplitude between the left and right earphones representing one imaginary dimension space and the difference in tone representing a different dimension in space.

6. An apparatus as in claim 5 wherein the second operator control means comprises a second control stick means for controlling the position of the audio tone within an imaginary audio space inside the subject's head, wherein the computer means records the left-right and up-down position of said second control stick means corresponding to the imaginary position of the audio tone.

7. An apparatus for testing and analyzing the evoked brain electrical activity and motor responses of a subject to simultaneous stimuli in two different modes, the apparatus comprising:
   a) a first means to present visual stimuli on a screen, the visual stimuli being intensity modulated at a first frequency in the range 3–40 Hz;
   b) a second means to present auditory stimuli to the subject, the auditory stimuli being intensity modulated at a second frequency in the range 3–40 Hz which is different from, and not a harmonic of, the first frequency;
   c) a plurality of EEG (electroencephalograph) sensors adapted to be removably attached to the subject's head for measuring analog brain wave electrical activity;
   d) amplification means to amplify the measured analog brainwave electrical activity;
   e) A/D (analog/digital) converter means to convert the amplified brain wave electrical activity to digital data;
   f) a first and a second operator control means, each being adapted to be controlled by the subject in response to the stimuli in two modes;
   g) a computer means for controlling the first means and second means for presenting to the subject the visual and auditory stimuli, for measuring the motor response of the subject to the visual and auditory stimuli, for recording the evoked brain wave digital data of the subject in response to the stimuli, including power spectral analysis of the evoked brain waves at the first and second frequencies, for comparing the motor responses and evoked brain wave digital data to a data base of normal test resulted stored in a memory of the computer means, and means for producing a display of the comparisons.

8. An apparatus as in claim 7 wherein the first and second operator control means are joy stick computer input devices.

9. An apparatus as in claim 7 wherein the A/D means is a variable gain analog-to-digital conversion means for digitizing the amplified analog brain wave electrical activity and wherein the variable gain of the A/D converter is controlled by the computer means.

10. An apparatus as in claim 7 wherein the screen displays a visible and movable target spot and a visible and movable tracking cursor, the target spot being controllable by the computer means and the cursor being controllable by the first operator control means; and wherein the auditory stimuli means includes means to produce an audio tone, a pair of headphones having left and right earphones for presenting the audio tone to the subject, the audio tone being controllable in amplitude and frequency by the computer means, the difference in amplitude between the left and right earphones representing one imaginary dimension space and differences in tone representing a different dimension in the space.

11. An apparatus as in claim 10 wherein the first operator control means comprises a control stick means for positioning the tracking cursor on the screen, the computer means receives the cursor movement signals from the control stick means and moves the cursor a corresponding distance on the screen, the second operator control means comprises a second control stick means for recording the position of the audio tone within an imaginary audio space inside the subject's head, and wherein the computer means records the left-right and up-down position of the second control stick means corresponding to the imaginary positions of the audio tone.

12. A method for testing and analyzing a test subject's evoked brain electrical activity and motor responses to visual and audio stimuli, comprising the steps of:

a) removably attaching a plurality of EEG (electroencephalograph) sensors to the subject's head;

b) presenting the subject with a moving target and a movable cursor on a video display screen;

c) recording the position of a first control stick, operated by the subject, which controls the position of the cursor on the video screen;

d) comparing the position of the cursor on the video screen with the position of the target on the video screen and calculating the number of touches of the cursor to the target scored by the subject and the time to obtain each of the touches;

e) presenting the subject with an audio tone stimuli and a follower sound through headphones;

f) varying the amplitude and frequency of the tone stimulus presented to the subject so that the position of the tone stimulus in an imaginary auditory space inside the subject's head moves left-right and up-down;

g) recording the position of a second control stick operated by the subject, which corresponds to the subject's attempt to follow the subject's perceived position of the audio tone with the follower sound;

h) comparing the left-right and up-down position of the second control stick with the left-right and up-down positions of the tone stimulus and calculating the number of touches the subject scores and the time to obtain each touch;

i) measuring the analog evoked brain wave electrical activity of the subject during application of the visual and audio stimuli;

j) amplifying the measured analog evoked brain wave electrical activity with a high gain amplification means;

k) digitizing the amplified analog evoked brain wave electrical activity in an analog-to-digital converter means;

l) analyzing the digitized evoked brain wave electrical activity in the computer means;

m) comparing the digitized brain wave electrical activity to a data base of normal brain wave responses stored in the memory of the computer means; and n) comparing the number of touches and times of the subject to obtain the touches to a data base of normal test results stored in the memory of the computer means.

13. A method as in claim 12 and further producing a visual output showing the results of the comparisons.

14. A method as in claim 13 wherein the visual output created by the apparatus is a topographical headmap of the test subject.

15. A method as in claim 13 wherein the visual output also includes a waveform representing the evoked brain wave electrical activity at a single electrode.

16. A method as in claim 13 wherein the visual output also includes a waveform representing the difference in evoked brain wave electrical activity at two electrodes.

17. A method as in claim 12 and further producing a visual output showing the reaction times of the subject required to score touches in response to the audio and visual stimuli.

18. A method as in claim 12 wherein the visual and audio stimuli are presented simultaneously.

19. A method as in claim 12 wherein the target, cursor, tone stimulus and follower sound are each intensity modulated at different frequencies from each other in the 3–40 Hz band.

* * * * *